United States Patent [19]

Cannata et al.

[11] Patent Number: 4,724,102
[45] Date of Patent: Feb. 9, 1988

[54] OPTICAL RESOLUTION OF RACEMIC MIXTURES OF ALPHA-NAPHTHYLPROPIONIC ACIDS AND DERIVATIVES OF SAID ACIDS

[75] Inventors: Vincenzo Cannata, Borgo Nuovo Pontecchio Marconi; Giancarlo Tamerlani, Pontecchio Marconi; Mauro Morotti, Marzabotto, all of Italy

[73] Assignee: Alfa Chemicals Italiana S.p.A., Milan, Italy

[21] Appl. No.: 844,834

[22] Filed: Mar. 27, 1986

[30] Foreign Application Priority Data

Apr. 18, 1985 [IT] Italy .................. 3407 A/85

[51] Int. Cl.⁴ .................. C07C 87/30; C07B 57/00
[52] U.S. Cl. .................. 260/501.15; 260/501.1; 562/402; 562/444; 562/466
[58] Field of Search .................. 562/401, 402, 444, 466; 260/501.15, 501.1

[56] References Cited

U.S. PATENT DOCUMENTS

| | | | |
|---|---|---|---|
| 3,683,015 | 8/1972 | Dyson | 562/401 X |
| 3,686,183 | 8/1972 | Dyson | 562/401 X |
| 3,904,683 | 9/1975 | Day et al. | 562/401 |
| 3,988,365 | 10/1976 | Gallegra | 562/401 |
| 4,246,164 | 1/1981 | Felder et al. | 562/401 X |
| 4,246,193 | 1/1981 | Holton | 562/401 X |
| 4,399,284 | 8/1983 | Cannata et al. | 562/401 X |

Primary Examiner—Howard T. Mars
Assistant Examiner—Vera C. Clarke
Attorney, Agent, or Firm—Bucknam and Archer

[57] ABSTRACT

A new process for the optical resolution of racemic mixtures of α-naphthylpropionic acids of formula

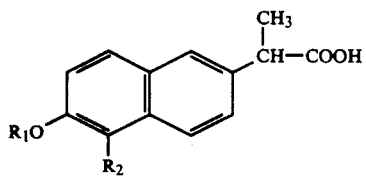

wherein $R_1$ is ($C_{1-6}$) alkyl and $R_2$ represents hydrogen or a halogen atom comprises reacting a racemic mixture of a compound of formula II

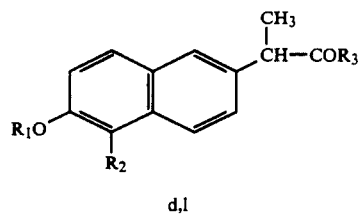

wherein $R_1$ and $R_2$ have the above seen meanings and $R_3$ is a reactive group, with an optically active aminoacid of formula

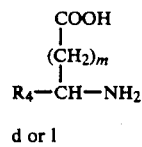

wherein $R_4$ represents a ($C_{1-8}$) alkyl, phenyl, substituted phenyl, benzyl, substituted benzyl or carboxy, and m is an integer from 0 to 4, to give a pair of diastereoisomeric amides of formula

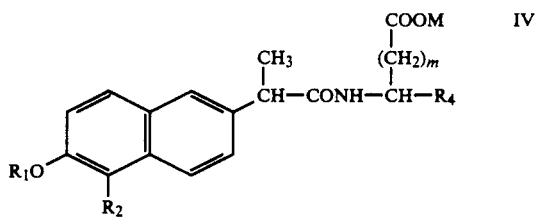

[d,d + l,d] or [d,l + l,l]

wherein $R_1$, $R_2$, $R_4$ and m have the above seen meanings, and M is a hydrogen atom or a cation of an alkali metal or a cation of an organic base. Compounds IV are resolved into the single diastereoisomeric amides d,d or l,d, or d,l or l,l. Acid hydrolysis gives the optically active compound I.

21 Claims, No Drawings

OPTICAL RESOLUTION OF RACEMIC MIXTURES OF ALPHA-NAPHTHYLPROPIONIC ACIDS AND DERIVATIVES OF SAID ACIDS

BACKGROUND OF THE INVENTION

The α-naphthylpropionic acids are known from the literature for their biological properties; owing to the presence of the asymmetric carbon atom bonded to the naphthyl nucleus, they can exist both in the form of racemic mixtures and in the form of the corresponding d or l optically active isomers.

The d isomer of the compound of formula I in which $R_1$ represents the methyl radical and $R_2$ represents a hydrogen atom, namely the d-2-(6-methoxy-2-naphthyl)-propionic acid described in U.S. Pat. No. 3,904,682 and internationally known as naproxen (INN-=International Nonproprietary Name), holds a noteworthy importance for its very good antiinflammatory properties.

Its preparation has been reported many times in the literature, mainly in the patent literature. Usually these methods contemplate the synthesis of d,l-2-(6-methoxy-2-naphthyl)-propionic acid, or a precursor thereof, and the subsequent resolution into the optical antipodes via formation of salts with optically active organic bases like cinchonidine, dehydroabietylamine, N-methyl-D-glucamine, N-alkyl-D-glucamines (see French Publication No. 2,035,846 and U.S. Pat. Nos. 3,683,015; 4,246,164; 4,246,193 and 4,423,244). All of these resolution methods possess more or less severe drawbacks. As an example, it is often necessary to carry out several recrystallizations for obtaining the salt of the desired isomer in the wanted purity degree; in addition, the purity degree of the mixture to be resolved remarkably influences the resolution itself.

The stereospecific synthesis of naproxen and, in general, of the optically active α-naphthyl-propionic acids (see European laid open application Nos. 81993 and 110671) has been tried for avoiding these drawbacks. To our experience, however, these procedures appear to involve a lot of problems, like the use of Grignard's reagents, the optical purity not always sufficiently high and the need to use optically active intermediates.

Therefore there is still the need of technically and economically valid resolution methods of the α-naphthylpropionic acids.

SUMMARY OF THE INVENTION

The present invention refers to a new process for the optical resolution of substantially racemic mixtures of α-naphthylpropionic acids of formula

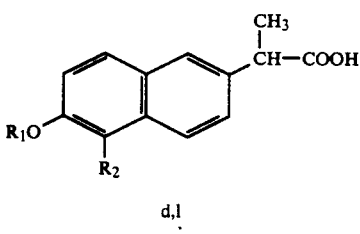

d,l

This process comprises reacting a substantially racemic mixture of a α-naphthylpropionic derivative of formula

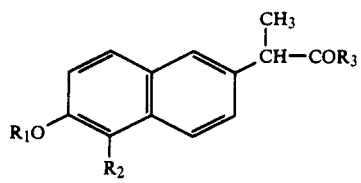

d,l with the d or l enantiomer of an aminoacid of formula

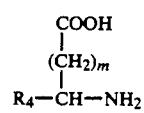

optionally in presence of a solvent or of a solvent system and of an organic or inorganic base, in order to obtain a pair of diastereoisomeric amides of formula

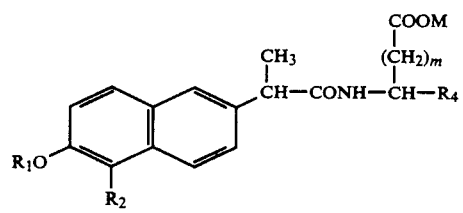

[d,d + l,d] or [d,l + l,l]

The pair of diastereoisomeric amides is then resolved in very high yields, which may be nearly quantitative in particular experimental conditions, into one of the single diastereoisomeric amides of formula

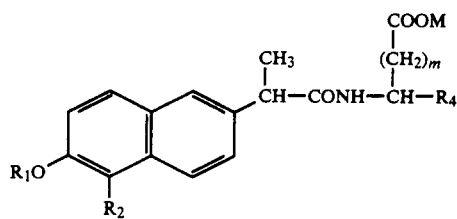

d,d or l,d or d,l or l,l optionally in the presence of an organic or inorganic base in a suitable solvent or solvent system.

This amide is subsequently transformed, by means of an acidic hydrolysis, into the desired optically active α-naphthylpropionic acid of formula

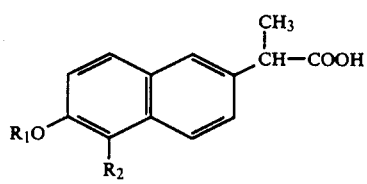

d or l

The process of the present invention can be illustrated by the following scheme:

SCHEME 1

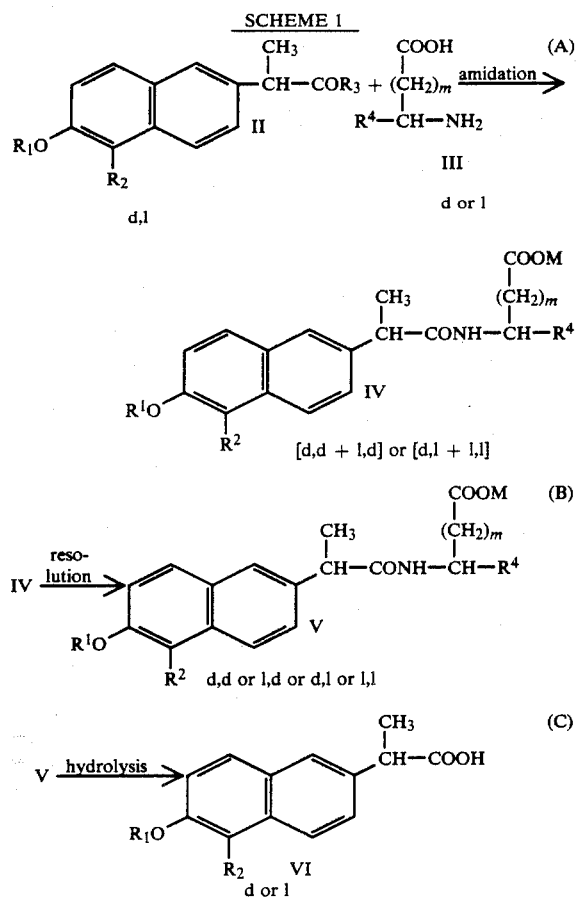

The amides of formula IV and V obtained in this process according to scheme 1 are new and therefore they constitute a further object of the present invention.

In the above formulas from I to VI, $R_1$ represents an alkyl radical, straight or branched, having from 1 to 6 carbon atoms; $R_2$ represents a hydrogen atom or a halogen atom; $R_3$ repesents a group selected from halogen, hydroxy, straight or branched alkoxy containing from 1 to 8 carbon atoms substituted by halogen or phenyl or both, straight or branched aliphatic acyloxy containing from 2 to 6 carbon atoms, benzoyloxy, substituted benzoyloxy, sulfonyloxy and benzensulfonyloxy, 4-methyl-benzene-sulfonyloxy, 2-imidazolyl-carbonyloxy; $R_4$ represents an alkyl radical, straight or branched, containing from 1 to 8 carbon atoms, carboxy group, a phenyl radical, a substituted phenyl radical, a benzyl radical, a substituted benzyl radical, M represents a hydrogen atom or a cation of an alkali metal or a cation of an organic base, and m represents an integer comprised between 0 and 4.

Furthermore, the first letter of each of the pairs of symbols d,d, l,d, d,l and l,l related to the diastereoisomeric amides of formula IV and V refers to the residue of the α-naphthylpropionic group, while the second letter refers to the residue of the aminoacid.

The starting substrate of formula II preferred for the fullfillment of the present invention is that in which $R_1$ is a methyl radical and $R_2$ is an atom of hydrogen or of bromine.

The preferred aminoacids of formula III are those in which $R_4$ represents a straight or branched alkyl radical containing from 1 to 4 carbon atoms carboxy and m is equal to 0, preferably aspartic acid or glutamic acid.

In practice a molar equivalent of a substantially racemic mixture of a compound of formula II is reacted with a molar equivalent of a d or l enantiomer of an aminoacid of formula III, optionally in presence of a solvent or a solvent system and of an organic or inorganic base at a temperature comprised between about 0° C. and the boiling temperature of the reaction mixture.

Many solvents are suitable for this reaction, for instance the aromatic hydrocarbons like benzene, toluene, nitrobenzene, the xylenes, the halogenated hydrocarbons containing from 1 to 4 carbon atoms like methylene chloride, carbon tetrachloride and 1,1,2,2-tetrachloroethane, mono- and di-alkylamides, tetrahydrofuran, dioxane, aliphatic ketones, acetonitrile and mixtures thereof with water.

Preferred solvents are the aliphatic ketones and their mixtures with water.

The temperature at which the amidation reaction is carried out may vary within wide limits, from about 0° C. to the boiling temperature of the reaction mixture depending on the used reagents.

It was observed that when in the starting substrate of formula II $R_3$ is a halogen the reaction runs satisfactorily at low temperature, preferably between about 0° C. and about 20° C. Moreover the presence of a strong base, organic or inorganic, preferably an hydroxide of an alkali metal, is necessary in order to buffer the acidity which forms during the reaction. The yields of these reactions are practically quantitative and in any case never lower than 80 percent.

A pair of diastereoisomeric amides of formula

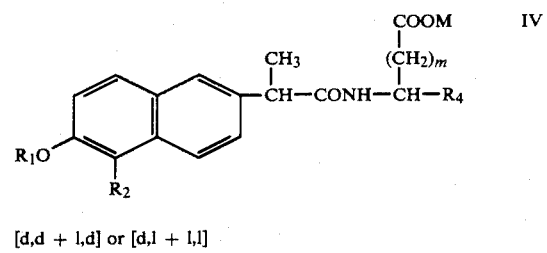

[d,d + l,d] or [d,l + l,l]

wherein $R_1$, $R_2$, $R_4$, M and m are as above defined, is formed, which, depending on whether the used optically active aminoacid is the d isomer or the l isomer, can be the pair [d,d+l,d] or the pair [d,l+l,l]. The so obtained pair of diastereoisomeric amides can be isolated and characterized, if desired, or the resolution into the single diastereoisomeric amides can directly take place on the raw reaction product according to step B of the scheme 1.

The resolution is performed by dissolving or suspending a pair of diastereoisomeric amides of formula IV, [d,d+l,d] or [d,l+l,l] in a suitable solvent or solvent system like, for instance, an aromatic hydrocarbon, an halogenated hydrocarbon containing from 1 to 4 carbon atoms, alcohols containing from 1 to 6 carbon atoms, mono- and di-alkylamindes, aliphatic ketones, glycols, monoethers of glycols, dioxane, acetonitrile, tetrahydrofuran, their mixtures with water or water.

The solution or suspension is heated at a temperature comprised between about 50° C. and the boiling temperature of the reaction mixture, optionally in the presence of an alkali base. The reaction mixture is then heated at the boiling temperature of the reaction mixture for a period of time comprised between 30 minutes and 24 hours, optionally distilling off from the reaction ambient the water possibly introduced in order to dissolve the alkali base.

Preferred solvents in the fullfillment of the resolution are the alcohols containing from 3 to 5 carbon atoms, in particular n-butanol, their mixtures with water or water. Preferred alkali bases are sodium and potassium hydroxides.

The amount of alkali base used may vary within wide ranges; preferably from about 1 to about 3 molar equivalents of alkali bases are used for each molar equivalent of the pair of the diastereoisomeric amides to be resolved. When the resolution reaction is carried out in water, one or more molar equivalents of an organic base, like for instance dibenzylamine, can be added at the end of the heating, so obtaining the crystallization of a salt of an organic base of the single diastereoisomeric amide.

Subsequently the crystallization is completed by cooling the reaction mixture and the single diastereoisomeric amide of formula V, in which M represents the cation of the used organic or inorganic base, may be recovered by filtering the crystallized solid and by subsequently washing and drying it. By treating said salt by means of an aqueous solution of an organic or inorganic acid, the amide of formula V precipitates in which M represents an atom of hydrogen. The single diastereoisomeric amides d,d or l,d or d,l or l,l obtained through the described resolution method can be further purified, for instance by recrystallization from suitable solvents, e.g. those employed in the resolution procedure.

The yield of single diastereoisomeric amide is exceptionally high in this process. In fact it is almost always higher than 70 percent, calculated over the starting pair of diastereoisomeric amides and not over the single diastereoisomeric amide contained in the pair. In other words, one molar amount of a pair of diastereoisomeric amides [d,d+l,d] or [d,l+l,l] is resolved with this process so as to provide not the maximum amount of the single diastereoisomer contained in the pair, namely 0.5 moles, but at least 0.7 moles. Moreover the fact that amides made of substantially racemic mixtures of α-naphthylpropionic acids with optically active d or l aminoacids could be resolved by fractional crystallization is totally new.

It must be pointed out that with the process described in the present invention it is possible to obtain the final precursors of the optically active α-naphthylporpionic acids of formula VI with yields absolutely higher than those obtained with the classical resolution methods known from the literature. In fact, in none of these procedures, all based on the formation of pairs of diastereoisomeric salts with optically active organic bases, the desired single diastereoisomeric salt is obtained with a yield higher than 50% calculated over the pair of diastereoisomeric salts which must be resolved.

In the process object of the present invention, the desired diastereoisomeric amide, precursor of the acid of formula VI, is obtained with a yield higher than 70% calculated over the pair of the starting diastereoisomeric amides.

Considering also that the yields of the subsequent hydrolysis (step C) are always higher than 80%, it is manifest that the present invention provides a new and useful method for the preparation of optically active α-naphthylpropionic acids.

To obtain the final compounds of formula VI, the single diastereoisomeric amide of formula V obtained as under step (B) is subjected to acid hydrolysis, for instance by heating it to the boiling for a period comprised between 3 and 24 hours, in the presence of aqueous solutions of mineral or organic acids or of mixtures thereof.

If necessary, the so obtained desired acid of formula VI may be subjected to further purification according to known techniques, in order to obtain it with the maximum purity degree.

When in the compounds of formula IV, V and VI $R_2$ represents an atom of halogen, it is possible to catalytically substitute it with a hydrogen atom, for instance by means of the hydrogenation procedure described in U.S. Pat. No. 4,423,244.

The following examples are provided for with the purpose of better illustrating the invention but have not to be considered as an its limitation.

The determination of the optical rotatory power was carried out by means of a Perkin Elmer 241 apparatus.

The starting substrates of formula II were prepared according to known literature methods.

The optically active aminoacids of formula III are commercial products or were prepared according to known literature methods.

EXAMPLE 1

N-[d,l-2-(5-Bromo-6-methoxy-2-naphthyl)-propionyl]-l-aspartic acid [d,l+l,l]

A solution of 78.3 g (0.239 moles) of the chloride of the d,l-2-(5-bromo-6-methoxy-2-naphthyl)-propionic acid in 180 ml of anhydrous acetone is slowly poured drop by drop, under strong stirring, into a solution of 31.87 g (0.239 moles) of D-(−)-aspartic acid in a mixture made by 180 ml of water and 47.88 ml (0.478 moles) of a 30% (w/w) aqueous solution of sodium hydroxide, while keeping the temperature at about 10° C. and the pH value at about 9.5 by means of a 15% (w/w) aqueous solution of sodium hydroxide. The reaction mixture is further stirred for one hour after the end of the dripping while raising the temperature at about 20° C., then it is filtered and the acetone is eliminated by evaporation under vacuum. The aqueous solution is acidified to pH 6.5 by means of a concentrated aqueous solution of hydrochloric acid and is sometimes washed with ethyl acetate. The traces of ethyl acetate remained into the aqueous solution are eliminated by evaporation under vacuum and subsequently the aqueous solution is addd with 150 ml of formic acid. The precipitate is extracted with methylbutylketone; the organic layer is first washed with water and then with 10% (w/v) aqueous solution of sodium sulfate, dried over sodium sulfate, filtered on decolorating earths and evaporated under vacuum to give 82 g of product, having $[\alpha]_D^{20} = +1.2°$ (C=1% in methanol), with a yield of 80.7% on theoretical.

EXAMPLE 2

N-[d,l-2-(5-Bromo-6-methoxy-2-naphthyl)-propional]-d-aspartic acid [d,d+l,d]

By substantially operating according to the modalities described in Example 1, by using the L-(+)-aspartic acid instead of the D-(−)-aspartic acid, the title product is obtained having $[\alpha]_D^{20} = -1.1°$ (C=1% in methanol).

EXAMPLE 3

N-[d-2-(5-Bromo-6-methoxy-2-naphthyl)-propionyl]-l-aspartic acid [d,l]

10.6 Grams (0.025 moles) of N-[d,l-2-(5-bromo-6-methoxy-2-naphthyl)-propionyl]-l-aspartic acid are dissolved in 100 ml of n-butanol by heating at 80° C. and then are added with 6.25 ml (0.063 moles) of a 30% (w/w) aqueous solution of sodium hydroxide. A suspension is obtained which is refluxed for 6 hours, then it is added with further 50 ml of n-butanol and it is further heated to reflux by eliminating the water by distillation until 117° C. are reached. The mixture is cooled to 20° C. and the precipitated solid is filtered and is collected and dissolved in 50 ml of water. The solution is filtered on decolorating earths, heated at about 80° C. and added with 50 ml of formic acid. The product crystallizes by cooling to about 40° C. and is washed on the filter with water. 7.5 Grams of product having m.p. 170°-172° C. and $[\alpha]_D^{20} = -10°.3$ (C=1% in methanol) are obtained with a yield of 70.7% over the pair of the starting diastereoisomeric amides.

EXAMPLE 4

N-[d-2-(5-Bromo-6-methoxy-2-naphthyl)-propionyl]-l-aspartic acid [d,l]

A solution of 65.52 g (0.20 moles) of the chloride of the d,l-2-(5-bromo-6-methoxy-2-naphthyl)-propionic acid in 100 ml of anhydrous acetone is slowly poured drop by drop, under strong stirring, into a solution of 26.60 g (0.20 moles) of D-(−)-aspartic acid in a mixture made by 100 ml of water and 40 ml (0.40 moles) of a 30% (w/w) aqueous solution of sodium hydroxide, while keeping the temperature at about 10° C. and the pH value at about 9.5 by means of a 15% (w/w) aqueous solution of sodium hydroxide. The acetone is distilled off under vacuum at the end of the dripping, when the pH value is stabilized at 9.5. The aqueous solution is then diluted with 100 ml of water, brought to pH 6.5 with concentrated aqueous hydrochloric acid, washed four times with ethyl acetate and lastly evaporated under vacuum to eliminate the traces of solvent. The aqueous solution is acidified to pH 2.5 by adding concentrated aqueous hydrochloric acid and is twice extracted with 100 ml of n-butanol. The combined organic layers are washed with water and heated to reflux to eliminate the water until the temperature of distillation exceeds 111° C. Then the reaction is cooled to about 80° C. and is added with further 600 ml of n-butanol and 50 ml of a 30% (w/w) aqueous solution of sodium hydroxide. The reaction mixture is heated to reflux for one hour and then the disodium salt of the N-[d-2-(5-bromo-6-methoxy-2-naphthyl)-propionyl]-l-aspartic acid crystallizes, which is filtered, washed on the filter with n-butanol and dried under vacuum, so obtaining 80.2 g with a yield of 85.6%.

61 Grams of said salt are dissolved in 250 ml of water at about 90° C. and added with 250 ml of formic acid. The N-[d-2-(5-bromo-6-methoxy-2-naphthyl)-propionyl]-l-aspartic acid begins to crystallize by cooling and at about 20° C. it is filtered and washed on the filter first with a 1:1 mixture of formic acid/water and then with water. After drying under vacuum, 38.3 g of pure product, having $[\alpha]_D^{20} = -10.2°$ (C=1% in methanol) and m.p. 170°-172° C., are obtained with a yield of 69.3% on theoretical.

The global yield of the whole process results to be 59.3% calculated over the starting chloride of the d,l-2-(5-bromo-6-methoxy-2-naphthyl)-priopionic acid.

EXAMPLE 5

N-[d-2-(5-Bromo-6-methoxy-2-naphthyl)-propionyl]-l-aspartic acid [d,l]

10 Grams (0.0235 moles) of N-[d,l-2-(5-bromo-6-methoxy-2-naphthyl)-propionyl]-l-aspartic acid are dissolved in 100 ml of n-butanol by heating at 80° C. and then are added with 3.83 g of 86% potassium hydroxide (0.0589 moles) dissolved in 6.2 ml of water. A suspension is obtained which is heated to reflux for one hour eliminating the water by distillation. Then the reaction mixture is cooled to about 20° C., the precipitated solid is filtered, is washed on the filter with n-butanol and is dried under vacuum obtaining 11.4 g of dipotassium salt of the N-[d-2-(5-bromo-6-methoxy-2-naphthyl)-propionyl]-l-aspartic acid with a yield of 96.7%. The salt is dissolved at about 80° C. in 50 ml of water and the solution is added with 50 ml of formic acid. The N-[d-2-(5-bromo-6-methoxy-2-naphthyl)-propionyl]-l-aspartic acid begins to crystallize by cooling. The suspension is filtered at about 20° C. and the solid is washed on the filtered with water. After drying under vacuum, 7.4 g of product, having the same chemical-physical characteristics as those of the product described in Example 4, are obtained with a yield of 74% calculated over the pair of the starting diastereoisomeric amides.

EXAMPLE 6 d-2-(5-Bromo-6-methoxy-2-naphthyl)-propionic acid

30 Grams (0.071 moles) of N-[d-2-(5-bromo-6-methoxy-2-naphthyl)-propionyl]-l-aspartic acid coming from Example 4 are suspended in a mixture made by 30 ml of water, 30 ml of glacial acetic acid and 17.6 ml of concentrated aqueous hydrochloric acid. The mixture is heated to reflux under stirring for about 4 hours and then is cooled to about 20° C. The crystallized solid is filtered, washed on the filter first with a 1:1 mixture of water/acetic acid and then with water and lastly it is dried under vacuum. 20.7 Grams of pure d-2-(5-bromo-6-methoxy-2-naphthyl)-propionic acid, having $[\alpha]_{578}^{20} = +46°$ (C=1% in chloroform), are obtained with a yield of 94.7% on theoretical.

EXAMPLE 7

N-[d,l-2-(5-Bromo-6-methoxy-2-naphthyl)-propionyl]-l-glutamic acid [d,l+l,l]

A solution of 114.3 g (0.349 moles) of chloride of the d,l-2-(5-bromo-6-methoxy-2-naphthyl)-propionic acid in 200 ml of anhydrous acetone is slowly poured drop by drop, under strong stirring, into a solution of 51.4 g (0.349 moles) of D-(−)-glutamic acid in a mixture made by 200 ml of water and 69.9 ml (0.699 moles) of a 30% (w/w) aqueous solution of sodium hydroxide, while keeping the temperature at about 10° C. and the pH value at about 9.5 by means of a 15% (w/w) aqueous solution of sodium hydroxide. After the end of the dripping, the reaction mixture is kept under stirring at 10° C. for one hour, then it is filtered and the acetone is eliminated by evaporation under vacuum. The aqueous solution is brought to pH 6.5 and washed sometimes with ethyl acetate. The traces of ethyl acetate remained in the aqueous solution are eliminated by evaporation under vacuum and then the aqueous solution is acidified to pH 2.0 constant by adding concentrated aqueous hydrochloric acid. The precipitated product is filtered, washed on the filter with water and dried under vacuum. 137.5 Grams of product, having $[\alpha]_D^{20} = +10°.9$ (C=1% in methanol) and m.p.=160°-161.5° C., are obtained, with a yield of 89.9% on theoretical.

EXAMPLE 8

N-[d,l-2-(5-Bromo-6-methoxy-2-naphthyl)-propionyl]-d-glutamic acid [d,d+l,d]

By substantially operating according to the modalities described in example 7, by employing the L-(+)-glutamic acid instead of the D-(−)-glutamic acid, the title product is obtained, having $[\alpha]_D^{20} = -11.4°$ (C=1% in methanol) and m.p. 160°-162° C.

EXAMPLE 9

N-[d-2-(5-bromo-6-methoxy-2-naphthyl)-propionyl]-l-glutamic acid [d,l]

20 Grams of N-[d,l-2-(5-bromo-6-methoxy-2-naphthyl)-propionyl]-l-glutamic acid are suspended in 200 ml of n-butanol and after heating to about 80° C. they are added with 11.5 ml of a 30% (w/w) aqueous solution of sodium hydroxide and the reaction mixture is heated to reflux for 3 hours. After slow cooling to about 20° C., the crystallized solid is filtered and is washed on the filter with n-butanol. After drying under vacuum 21.6 g of disodium salt of the N-[d-2-(5-bromo-6-methoxy-2-naphthyl)-propionyl]-l-glutamic acid are obtained. Said salt is dissolved in 200 ml of water, the solution is filtered on decolorating earths, brought to 100° C. and then added with formic acid to pH 3.0. After slow cooling to 0° C., the crystallized solid is filtered, is washed with water and is dried under vacuum. 18.2 Grams of pure product, having $[\alpha]_D^{20} = +15.2°$ (C=1% in methanol) and m.p. 144°-147° C., are obtained with a yield of 91% calculated over the starting pair of the diastereoisomeric amides.

EXAMPLE 10

N-[d-2-(5-Bromo-6-methoxy-2-naphthyl)-propionyl]-l-glutamic acid [d,l]

A solution of 65.52 g (0.20 moles) of chloride of the d,l-2-(5-bromo-6-methoxy-2-naphthyl)-propionic acid in 100 ml of anhydrous acetone is slowly poured drop by drop, under strong stirring, into a solution of 29.40 g (0.20 moles) of D-(−)-glutamic acid in a mixture made by 100 ml of water and 40 ml (0.40 moles) of a 30% (w/w) aqueous solution of sodium hydroxide, while keeping the temperature at about 10° C. and the pH value at about 9.5 by means of a 15% (w/w) aqueous solution of sodium hydroxide. At the end of the dripping, when the pH value is stabilized at 9.5, the aceton is distilled off under vacuum. Then the aqueous solution is diluted with 100 ml of water, brought to pH 6.5 with concentrated aqueous hydrochloric acid, washed three times with ethyl acetate and lastly evaporated under vacuum in order to eliminate the traces of solvent.

The aqueous solution is then acidified at pH 2.5 with concentrated aqueous hydrochloric acid and twice extracted with 200 ml of n-butanol. The combined organic layers are washed with a 10% aqueous solution of sodium sulfate and then heated to reflux in order to eliminate the water until the temperature of distillation exceeds 108° C. Then the reaction mixture is cooled to about 80° C. and is added with further 400 ml of n-butanol and 50 ml of a 30% (w/w) aqueous solution of sodium hydroxide. The reaction mixture is heated to reflux for another hour, again eliminating water until the temperature of distillation reaches 100° C. and then is cooled to about 20° C. so as the disodium salt of the N-[d-2-(5-bromo-6-methoxy-2-naphthyl)-propionyl]-l-glutamic acid crystallizes and it is filtered, washed on the filter with n-butanol and dried under vacuum, obtaining 92.4 g with a yield of 95.8%.

50 Grams of said salt are dissolved at about 90° C. in 200 ml of water, added with 200 ml of formic acid and heated to reflux. The N-[d-2-(5-bromo-6-methoxy-2-naphthyl)-propionyl]-l-glutamic acid begins to crystallize by cooling and at 20° C. is filtered and washed on the filter first with a 1:1 mixture of water/formic acid and then with water. After drying under vacuum 35 g of pure product having $[\alpha]_D^{20} = +15.4°$ (C=1% in methanol) and m.p. 145°-147° C., are obtained with a yield of 77%. The overall yield of the whole process results to be 73.8% in respect of the chloride of the starting d,l-2-(5-bromo-6-methoxy-2-naphthyl)-propionic acid.

EXAMPLE 11 d-2-(5-Bromo-6-methoxy-2-naphthyl)-propionic acid

30 Grams (0.069 moles) of N-[d-2-(5-bromo-6-methoxy-2-naphthyl)-propionyl]-l-glutamic acid are suspended in a mixture of 30 ml of water, 30 ml of acetic acid and 17.1 ml of concentrated hydrochloric acid and the reaction mixture is heated to reflux for 14 hours. Then the reaction mixture is cooled to about 20° C., the precipitated solid is filtered, is first washed with a 1:1 mixture of acetic acid/water and then with water and is dried under vacuum. 17.3 Grams of chromatographically pure product, having $[\alpha]_{578}^{20} = +45.2°$ (C=1% in chloroform) are obtained with a yield of 81.1% on theoretical.

EXAMPLE 12

N-[d-2-(5-bromo-6-methoxy-2-naphthyl)-propionyl]-d-glutamic acid, dibenzylamine salt [d,d]

20 Grams (0.0456 moles) of N-[d,l-2-(5-bromo-6-methoxy-2-naphthyl)-propionyl]-d-glutamic acid are suspended in 100 ml of water, are added with 4.56 ml (0.0456 moles) of a 30% (w/w) aqueous solution of sodium hydroxide and the reaction mixture is heated to reflux till to get a complete solubilization. The solution is added with 8.73 ml (0.0456 moles) of dibenzylamine and then is cooled to 90° C. and the crystallization is seeded by means of a little amount of pure dibenzylamine salt of the N-[d-2-(5-bromo-6-methoxy-2-naphthyl)-propionyl]-d-glutamic acid. After cooling to ambient temperature, the suspension is diluted with 100 ml of water, is cooled to 0° C. and is filtered. The solid is washed on the filter with water and dried under vacuum to give 16.2 g of the pure title compound, with a yield of 85.3% calculated over the amount of the d,d diastereoisomeric amide contained in the pair of diastereoisomeric amides. This product shows $[\alpha]_D^{20} = +4.7°$ (C=1% in methanol) and m.p. 159°-163° C.

EXAMPLE 13

N-[d-2-(5-bromo-6-methoxy-2-naphthyl)-propionyl]-d-glutamic acid [d,d]

15 Grams of the dibenzylamine salt of the N-[d-2-(5-bromo-6-methoxy-2-naphthyl)-propionyl]-d-glutamic acid are suspended in 150 ml of water and in 100 ml of methylene chloride and are slowly added, under stirring, with a 30% (w/w) aqueous solution of sodium hydroxide till to obtain a complete solubilization. The biphase solution is filtered through decolorating earths and then the two phases are separated. The organic layer is thrown away while the aqueous layer is washed with 50 ml of methylene chloride, heated at about 90° C. and acidified to pH 3.0 by means of formic acid. After cooling to about 20° C., the suspension is filtered and the solid is washed on the filter with water and dried under vacuum obtaining 7.5 g of pure product, having $[\alpha]_D^{20} = -7.9°$ (C=1% in methanol) and m.p. 175°-176° C., with a yield of 96% on theoretical.

EXAMPLE 14 d-2-(5-Bromo-6-methoxy-2-naphthyl)-propionic acid 4.38 Grams (0.01 moles) of N-[d-2-(5-bromo-6-methoxy-2-naphthyl)-propionyl]-d-glutamic acid are hydrolized according to the modalities reported in Example 11 by using amounts of reagents proportionally correlated. 2.6 Grams of chromatographically pure product, having $[\alpha]_{578}^{20} + 46.3°$, (C=1% in chloroform) are obtained with a yield of 84% on theoretical.

We claim:

1. A process for the optical resolution of a racemic mixture of α-naphthylpropionic acids of formula

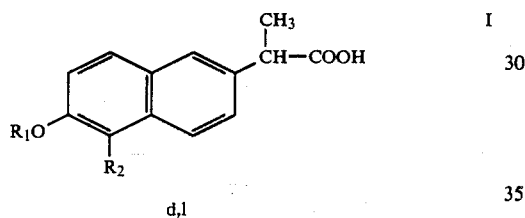

d,l wherein $R_1$ is methyl, $R_2$ is hydrogen or bromine which comprises the steps of:

(A) reacting a substantially racemic compound of formula

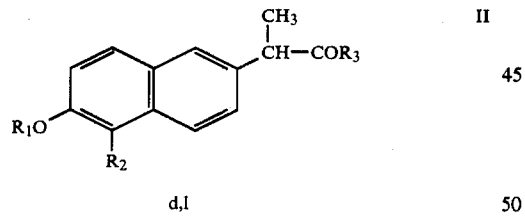

d,l wherein $R_1$ and $R_2$ are as above defined and $R_3$ is selected from the group consisting of halogen, hydroxy, straight or branched alkoxy containing from 1 to 8 carbon atoms substituted by halogen or phenyl or both, straight or branched aliphatic acyloxy, containing from 2 to 6 carbon atoms, with the d or l enantiomer of an aminoacid of formula

wherein $R_4$ is (1) a straight or branched alkyl radical containing from 1 to 4 carbon atoms, (2) phenyl, (3) substituted phenyl, (4) benzyl, (5) substituted benzyl, or (6) a carboxy and m is 1 or 2 when $R_4$ is carboxy and m is 0-4 when $R_4$ is as defined in (1), (2), (3), (4), or (5), in the presence of an organic or inorganic base and a solvent or solvent system which is a member selected from the group consisting of aromatic hydrocarbons, halogenated hydrocarbons containing from 1 to 4 carbon atoms, mono- or di-alkyl amides, glycols, monoethers of glycols, tetrahydrofuran, dioxane, aliphatic ketones, acetonitrile, mixtures thereof with water, in the presence of an organic or inorganic base at a temperature between 0° C. and the boiling temperature of the reaction mixture, whereby a pair of diastereoisomeric amides of formula

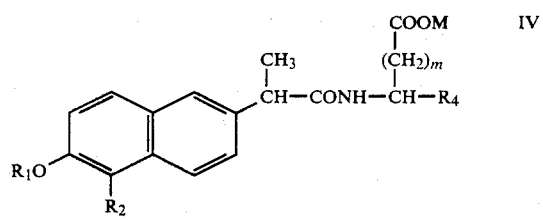

[d,d + l,d] or [d,l + l,l]

is obtained; wherein $R_1$, $R_2$, $R_4$ and m are defined as above and M is hydrogen, a cation of an alkali metal or a cation of an organic base;

(B) resolving said pair of diastereoisomeric amides in a single diastereoisomeric amide by heating at a temperature between 50° C. and the boiling temperature of the reaction mixture a molar amount of the pair of the diastereoisomeric amides in a solvent or solvent system, which is a member selected from the group consisting of alcohols of 1 to 6 carbon atoms, aromatic hydrocarbons, halogenated hydrocarbons containing from 1 to 4 carbon atoms, mono- or dialkyl amides, glycols, glycol monoethers, tetrahydrofuran, dioxane, aliphatic ketones, acetonitrile, mixtures thereof with water and water, for a period of time between 30 minutes and 24 hours, and then cooling the reaction mixture, whereby the desired single diastereoisomeric amide of formula

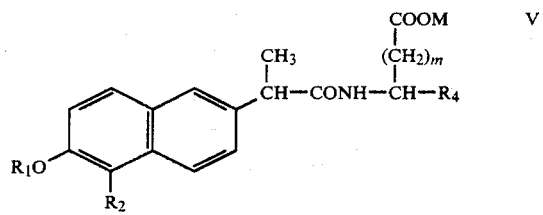

d,d or l,d or d,l or l,l wherein $R_1$, $R_2$, $R_4$, M and m are defined as above, crystallizes out and filtering off said compound of formula V, and when M is other than hydrogen, treating said compound of formula V with an aqueous solution of an organic or inorganic acid; and (c) subjecting the so obtained single diastereoisomeric amide to acid hydrolysis, by heating to the boiling point for 3-24 hours in the presence of an aqueous solution of an organic or a mineral acid or mixtures thereof, whereby a compound of formula

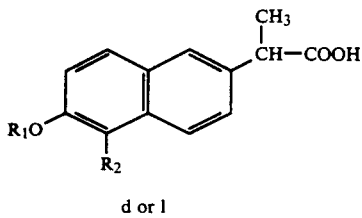

d or l is obtained, whereby $R_1$ and $R_2$ are as defined hereinabove and when in the compounds of formula IV, V or VI $R_2$ is bromine, reducing said compound of formula VI catalytically whereby the d or l form of said compound of formula I is obtained.

2. The process as defined in claim 1, wherein, in the compound of formula III, $R_4$ is carboxy and m is 1 or 2.

3. The process as defined in claim 2, wherein the aminoacid of formula III as aspartic acid or glutamic acid.

4. The process as defined in claim 1, wherein the compounds of formula II and III are employed in equimolecular amounts.

5. The process as defined in claim 4, wherein the solvent in step (A) is an aliphatic ketone or mixtures of aliphatic ketones with water.

6. The process as defined in claim 5, wherein step (B) is carried out in the presence of an alkali base which is a member selected from the group consisting of hydroxides of sodium and potassium.

7. The process according to claim 1 wherein step (B) is carried out in an alcohol of 3–5 carbon atoms, mixtures of alcohols of 3–5 carbon atoms and water or water.

8. The process as defined in claim 1, wherein step (C) is carried out in a mixture of acetic acid, hydrochloric acid and water.

9. The process according to claim 1 wherein M is a cation of an organic base and is the dibenzylammonium ion.

10. Pairs of diastereoisomeric amides of formula

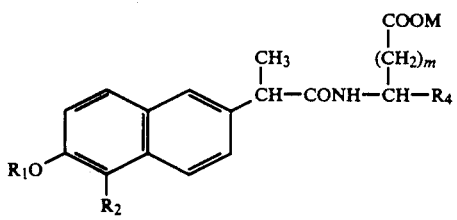

[d,d + l,d] or [d,l + l,l]

wherein $R_1$ is straight chain or branched alkyl of 1–6 carbon atoms, $R_2$ is hydrogen or halogen, $R_4$ is (1) straight chain or branched $C_{1-8}$ alkyl, (2) phenyl, (3) benzyl, or (4) COOH and m is an integer from 0 to 4 and when $R_4$ is —COOH, m is 1 or 2, and M is hydrogen, a cation of an alkali metal, or a cation of an organic base. 1.

11. A compound according to claim 10 which is the N[d,l-2-(5-bromo-6-methoxy-2-naphthyl)-propionyl]-l-aspartic acid.

12. A compound according to claim 10 which is the N-[d,l-2-(5-bromo-6-methoxy-2-naphthyl)-propionyl]-d-aspartic acid.

13. A compound according to claim 10 which is the N-[d,l-2-(5-bromo-6-methoxy-2-naphthyl)-propionyl]-l-glutamic acid.

14. A compound according to claim 10 which is the N-d,l-2-(5-bromo-6-methoxy-2-naphthyl)-propionyl]-d-glutamic acid.

15. The pair of diastereoisomeric amides according to claim 10 wherein M is the cation of an organic base and is the dibenzylammonium ion.

16. Diasteroisomeric amides of formula

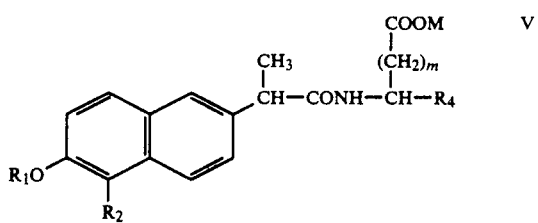

d,d or l,d or d,l or l,l wherein $R_1$ is straight chain or branched alkyl of 1–6 carbon atoms, $R_2$ is hydrogen or halogen, $R_4$ is (1) straight chain or branched $C_{1-8}$ alkyl, (2) phenyl, (3) benzyl, or (4) COOH and m is an integer from 0 to 4 and when $R_4$ is —COOH, m is 1 or 2, and M is hydrogen, a cation of an alkali metal, or a cation of an organic base. 1.

17. A compound according to claim 16 which is the N-[d-2-(5-bromo-6-methoxy-2-naphthyl)-propionyl]-l-glutamic acid.

18. A compound according to claim 16 which is the N-[d-2-(5-bromo-6-methoxy-2-naphthyl)-propionyl]-d-glutamic acid.

19. A compound according to claim 16 which is the N-[d-2-(5-bromo-6-methoxy-naphthyl)-propionyl]-d-glutamic acid, dibenzylamine salt.

20. A compound according to claim 16 which is the N-[d-2-(5-bromo-6methoxy-2-naphthyl)-propionyl]-l-aspartic acid.

21. The diastereoisomeric amides according to claim 16 wherein M is the cation of an organic base and is the dibenzylammonium ion.

* * * * *